United States Patent [19]

Petersen

[11] Patent Number: 5,569,260
[45] Date of Patent: Oct. 29, 1996

[54] DISTAL FEMORAL RESECTOR GUIDE

[76] Inventor: Thomas D. Petersen, 9680 Alto Dr., La Mesa, Calif. 91941

[21] Appl. No.: 353,225
[22] Filed: Dec. 1, 1994
[51] Int. Cl.$^6$ .................................................. A61B 17/15
[52] U.S. Cl. .............................................. 606/88; 606/87
[58] Field of Search ................................ 606/86, 87, 88, 606/89, 96, 97, 98

[56] References Cited

U.S. PATENT DOCUMENTS

| | | | |
|---|---|---|---|
| 4,773,407 | 9/1988 | Petersen | 606/88 |
| 4,907,578 | 3/1990 | Petersen | 606/88 |
| 5,049,149 | 9/1991 | Schmidt | 606/88 |
| 5,141,512 | 8/1992 | Farmer et al. | 606/89 |
| 5,364,401 | 11/1994 | Farrante et al. | 606/88 |
| 5,395,377 | 3/1995 | Petersen et al. | 606/88 |
| 5,451,228 | 9/1995 | Johnson et al. | 606/88 |

Primary Examiner—Gary Jackson
Assistant Examiner—Scott B. Markow
Attorney, Agent, or Firm—H. Jay Spiegel

[57] ABSTRACT

A distal femoral resector guide includes a generally T-shaped body with a saw guide at the distal end and a proximal stem structure. A rod extends from the saw guide and is intended to engage the intercondylar notch. The stem structure may be adjusted in length and includes a proximal end which may be shifted anteriorly and posteriorly with respect to the rest of the stem structure to accommodate distal femurs of differing configurations. A site line may be formed on the top surface of the stem structure and saw guide which includes an elongated groove filled with a material such as oxides of titanium which will glow under the presence of strong light. The inventive guide may be used in conjunction with a laser alignment mechanism to improve the accuracy of resection.

10 Claims, 4 Drawing Sheets

DISTAL FEMORAL RESECTOR GUIDE

BACKGROUND OF THE INVENTION

The present invention relates to an improved distal femoral resector guide. Applicant herein is the patentee of prior U.S. Pat. Nos. 4,773,407 and 4,907,578. These patents teach method and instruments for resection of the distal femur. These instruments have proven effective in orthopedic surgery. However, in order to utilize the instruments in Applicant's prior patents, it was necessary to form a flat plane on the superior femoral cortex to receive the base of the instrument. In this regard, reference is made to FIG. 1 herein which corresponds to FIG. 5 in each of Applicant's prior above-mentioned patents. FIG. 1 herein shows the distal end of the femur 10 with the reference numeral 11 referring to the flat plane which has been formed on the anterior femoral cortex through filing or other means. Reference numeral 15 shows the portion of the distal femur which is to be resected using the instrument disclosed therein as well as herein with the reference numeral 13 depicting the distal surface of the femur which is created when the portion 15 thereof is resected.

With reference, now, to FIG. 2, a normal, healthy, unresected distal femur is designated by the reference numeral 20 and is seen, in particular, to include condyles 21 and 23 which form a notch 25 therebetween at the anterior femoral cortex thereof.

With reference to FIG. 3, a corresponding view of the distal femur 20' is shown with the distal femur 20' also including condyles 21' and 23'. In FIG. 3, note the build-up of osteophytic bone on both anterior femoral condyles. The distal femur 20' exhibits osteophytic build-up generally designated by the reference numeral 27 which is evidence of advanced arthritis of the bone at that region. As is clear from comparing FIGS. 2 and 3, the osteophytic build-up obscures the notch which normally exists at the anterior femoral cortex. Such build-up renders the installation of a total knee prosthesis more difficult. As such, a need has developed for a distal femoral resector guide which can accommodate to the osteophytic build-up of arthritic bone on the distal femur, which device may be employed with reduced invasiveness as compared to the prior art.

As is known, in resecting the distal femoral condyles, the resection plane must be perpendicular to the mechanical axis of the femur in the transverse plane while also being perpendicular to the anterior femoral cortex in the sagittal plane. As is known, aligning a resection in these two planes is difficult. In the current state of the art, two methods have been employed to attempt to precisely determine the appropriate alignment of the distal femoral resection with respect to the transverse and sagittal planes. These methods employ either extramedullary alignment means or intramedullary alignment means. Each of these methods inherently includes its own inaccuracies.

In the case of the extramedullary means, the center of the femoral head has to be radiologically determined and marked externally on the patient. The use of trial and error to find the center of the femoral head and accurately locate the external marker on the patient is time consuming. Also, improper positioning of the x-ray machine directly over the center of the femoral head introduces the error factor known as "parallax". Also, alignment rods presently used have to be extended away from the center of the rotation of the bone and, consequently, there can be a significant error with any rotation of the distal femur from neutral. For these reasons, extramedullary alignment of the distal femoral cut fell out of favor in the late 1980s and the intramedullary rod has become popular.

With the intramedullary rod, a rod is placed through a drill hole in the intracondylar notch into the femoral canal and a predetermined difference between the anatomical axis of the femur and the mechanical axis, the so-called tibial femoral angle, is dialed in by a mechanical means and the perpendicular cut is then made through the transverse axis. Unfortunately, there are a number of inherent errors of the intramedullary alignment means. Not uncommonly, the intramedullary canal is quite large and the rod can be misaligned up against one cortex or the other. An error in a large intramedullary canal can be up to 2–3 degrees. Because the intramedullary rod is hidden from the surgeon's view, he has no way of determining this inherent error. Also, the intramedullary canal on the sagittal plane is curvalinear, and can cause mispositioning of the rod depending upon the entrance hole, either in the anterior or posterior direction, affording the rod an inaccurate means of determining a perpendicular cut to the femur in the sagittal plane.

Applicant has discovered that the only reliable way to make a perpendicular cut to the anterior femoral cortex in the sagittal plane is to locate the distal femoral cutter off the anterior femoral cortex. This task is particularly difficult to do unless the anterior femoral cortex cut is made first and indexed from the anterior femoral cortex. This requires a separate cutter which most systems incorporate. However, if there were a means to key the sagittal plane of the distal femoral resector off the anterior femoral cortex without the need to resect the anterior femoral cortex, this task could be accomplished by a single instrument.

However, there are two major problems to overcome. The first is the fact that, as explained above, on some knees there is a large osteophytic build-up of bone over the anterior femoral condyles. The anterior femoral cortex can be almost ½ inch lower than the anterior femoral condyles. Secondly, this build-up of osteophytic bone varies in distance from the intercondylar notch to the anterior femoral cortex depending on the size of the patient. Therefore, there must be an ability of the instrument to extend beyond the osteophytic build-up and to get down to the plane of the anterior femoral cortex.

It is with these problems in mind that the present invention was developed.

SUMMARY OF THE INVENTION

The present invention relates to an improved distal femoral resector guide. The present invention includes the following interrelated objects, aspects and features:

(A) In a first aspect, the inventive resector guide is of generally T-shaped configuration having a stem structure with a perpendicular saw guide attached thereto.

(B) The saw guide includes two parallel slots therethrough which are designed to permit the surgeon to decide whether he or she wishes to make a conservative or more aggressive resection of the distal femoral condyles depending upon the clinical situation involved. On the underside of the saw guide, a pin extends therefrom which is designed to engage the distal femoral intercondylar notch to allow accurate positioning of the instrument. On a proximal surface of the saw guide, angulated pin receiving openings are employed with their angulation being provided to prevent pins from backing out of the distal femur after installation.

(C) The stem structure has proximal and distal ends and includes a first portion adjacent the saw guide including first adjustment means for controllably elongating the stem structure. In particular, this first adjustment means includes telescoping structure as well as a pin guided in a slot to maintain rotative alignment of the stem structure with the saw guide. The adjustable elongation is in the proximal-distal direction along the femur. The saw guide is attached to the stem structure at the distal end thereof.

(D) Proximal of the adjustable elongation structure, a second adjustment means is provided allowing the proximal end of the stem structure to be adjusted with respect to the distal end thereof in the anterior-posterior direction. As will be understood in greater detail hereinafter, these two adjustment structures permit attachment of the inventive resector guide on the distal femur in a non-invasive manner and taking into account osteophytic build-up on the anterior femoral cortex. Bone engaging surfaces of the proximal and distal ends of the stem structure are convexly radiused in a direction perpendicular to a direction of elongation of the stem structure to provide line contact with the bone regardless of the slope of the anterior femoral cortex which normally slopes posteriorly about 15° on the medial side. These radiused surfaces facilitate use of the instrument on a left or right femur without loss of accuracy.

(E) In a further aspect, an elongated groove is provided in the proximal-distal direction which extends from the stem structure and over a top surface of the saw guide. This groove is preferably filled with a material such as oxides of titanium which glow in the presence of strong light such as that which is emitted by a laser device. This groove filled with an oxide of titanium may be employed in conjunction with a laser alignment device to assure accurate alignment of the inventive resector guide in the proximal-distal direction.

(F) In a further aspect, the proximal end of the stem structure may be provided with two lateral pins which may be used to receive an extramedullary alignment device such as that which is disclosed in Applicant's prior U.S. Pat. No. 4,907,578. Of course, the alignment device disclosed in both of Applicant's prior abovementioned United States Patents which employs the guide slot as an attachment means may also be suitably employed.

Accordingly, it is a first object of the present invention to provide an improved distal femoral resector guide.

It is a further object of the present invention to provide such a device including a stem structure having adjustments in the proximal-distal direction as well as in the anterior-posterior direction.

It is a still further object of the present invention to provide such a device including a saw guide having two parallel guide slots.

It is a yet further object of the present invention to provide such a device including angulated pin receiving openings on the proximal end of the saw guide.

It is a still further object of the present invention to provide such a device including an elongated groove designed to be used to guide proper alignment of the inventive device.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 4:
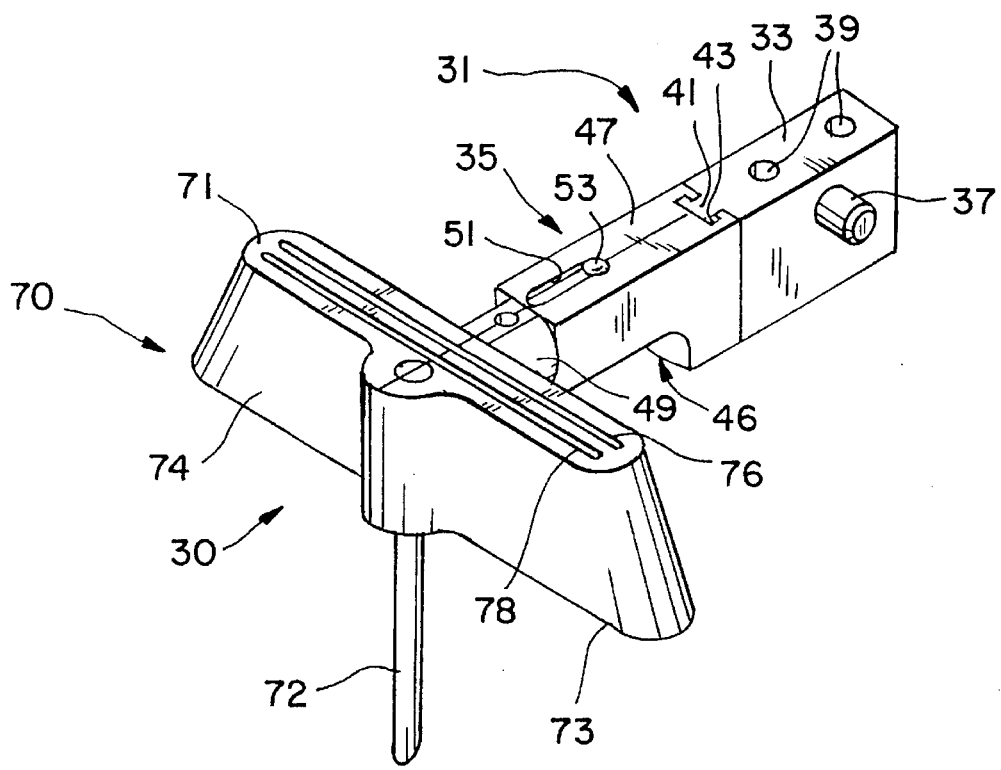
FIG. 4 shows a perspective view of the present invention looking in the proximal direction.
Figure 5:
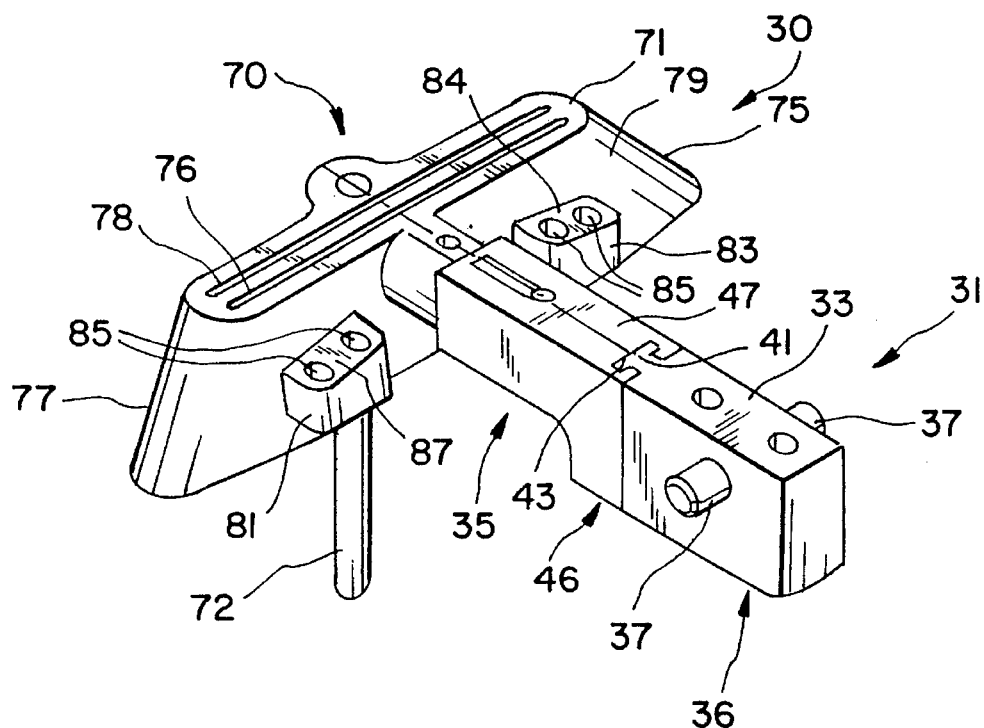
FIG. 5 shows a perspective view of the present invention looking in the distal direction.

With reference, first, to FIGS. 4 and 5, the inventive distal femoral resector guide is generally designated by the reference numeral 30 and is seen to include a stem structure 31 and a saw guide 70 attached at a distal end thereof. With particular reference to FIGS. 4 and 5, the stem structure 31 includes a proximal portion 33 and a distal portion 35. The proximal portion 33 includes laterally extending pins 37 which are designed to allow coupling of the device 30 with an extramedullary alignment device such as that which is disclosed in Applicant's prior U.S. Pat. No. 4,907,578. The proximal portion 33 further includes pin receiving openings 39 through which pins (not shown) may be inserted when the device 30 is installed on the distal femur. The proximal portion 33 includes T-shaped interlocking structure 41 on its distal end designed to couple with a T-shaped recess 43 formed in the proximal end of the distal stem structure 35. The proximal portion 33 is coupled to the distal stem portion 35 through frictional interaction between the elements 41 and 43. In this way, as seen, for example, in FIG. 9, the proximal portion 33 may be aligned in the anterior-posterior direction with respect to the distal portion 35 and the frictional interaction between the elements 41 and 43 will cause the portions 33 and 35 to be maintained in the position into which they are placed by the surgeon. The proximal portion 33 has, with reference to FIG. 10, a bone engaging surface 36 which is arcuate and convex, defined, for example, by a radius of curvature of 0.625". A corresponding surface 46 on the proximal end 47 of the distal portion 35 of the stem structure 31 (FIGS. 4 and 5) is correspondingly arcuate. The surfaces 36, 46 provide line contact with the bone surface regardless of the slope of the anterior femoral cortex which is known to slope posteriorly approximately 15° on the medial side. The surfaces 36, 46 facilitate the use of the instrument 30 for the left and right femur without loss of accuracy.

With reference back to FIGS. 4 and 5, the distal portion 35 of the stem structure 31 has, itself, proximal and distal ends. Thus, the proximal end 47 includes an internal passageway (not shown) which telescopingly receives the distal end 49 thereof. The distal end 49 of the distal portion 35 of the stem structure 31 is integrally attached to the saw guide 70.

As seen in FIGS. 4 and 5, the portion 47 of the distal portion 35 has an elongated slot 51 in a top surface thereof which receives a pin 53 integrally formed with the distal end 49. As the distal portion 35 of the stem structure 31 is extended and retracted, the pin 53 slides within the slot 51 to maintain rotative alignment of the stem structure 31 with respect to the saw guide.

With reference to FIGS. 4–9, the saw guide 70 includes a top surface 71, a bottom surface 73 which is wider than the top surface 71 and side walls 75, 77 interconnecting the top surface 71 and bottom surface 73. With reference to FIG. 5, the saw guide 70 also includes a proximal surface 79 on which are formed two proximally extending blocks 81, 83 through which pin receiving openings 85 are provided. As should be understood from FIG. 5, the blocks 81 and 83 are angled with respect to the plane of the top surface 71 of the saw guide 70 with the openings 85 extending perpendicular to the angled top surfaces 87, 89, respectively, of the blocks 81 and 83 and at an oblique angle to a line perpendicular to the top surface 71, such that pins (not shown) extending through the openings 85 will enter bone structure at an oblique angle. This angulation is provided to best facilitate retention of the pins within the distal femur after installation. In the preferred embodiment of the present invention, the openings 85 are angulated between 5 and 9 degrees toward the midline to provide cross-fixation of the pins into the bone to prevent lift-off and provide better accuracy of the resection.

As best seen in FIG. 4, a pin 72 extends in the posterior direction distal of the distal surface 74 of the saw guide 70. The pin 72 is intended to engage the distal femoral intracondylar notch to assist in positioning and aligning the instrument 30.

As particularly seen in FIGS. 4, 5, 6 and 7, the saw guide 70 includes first and second guide slots 76 and 78. Each guide slot or cutting slot is a precision slot having a thickness of only 0.002–0.004 greater than the thickness of a saw blade to increase the accuracy of the resection of the distal femoral condyles. Two slots 76 and 78 are provided to permit the surgeon to decide whether to make a conservative resection or a more aggressive resection on the distal femoral condyles, depending upon the clinical situation involved.

Figure 6:
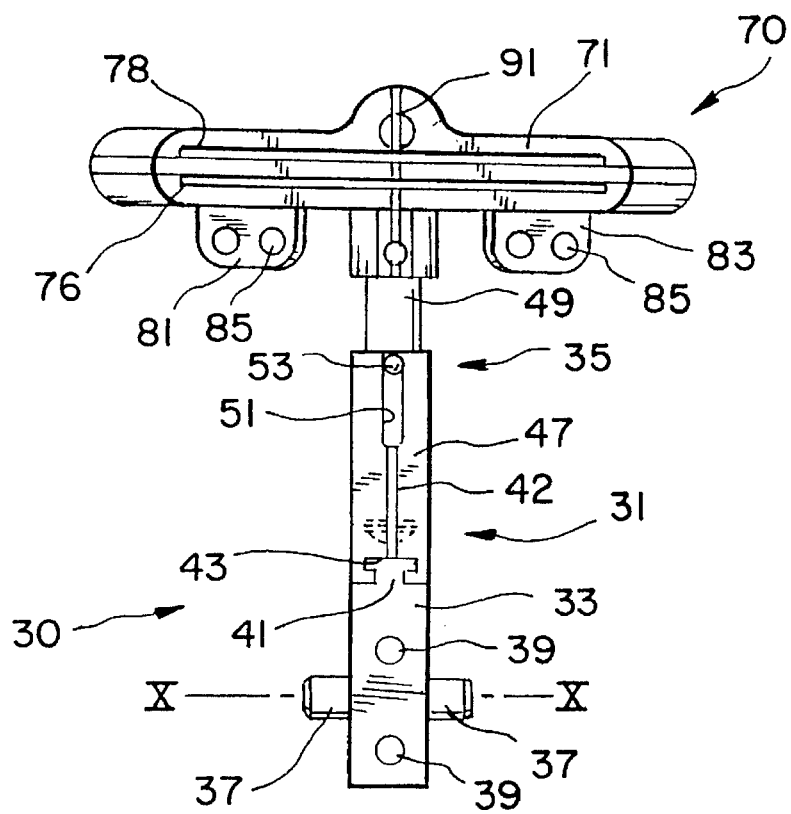
FIG. 6 shows a top view of the present invention with the stem structure in the extended configuration.
Figure 7:
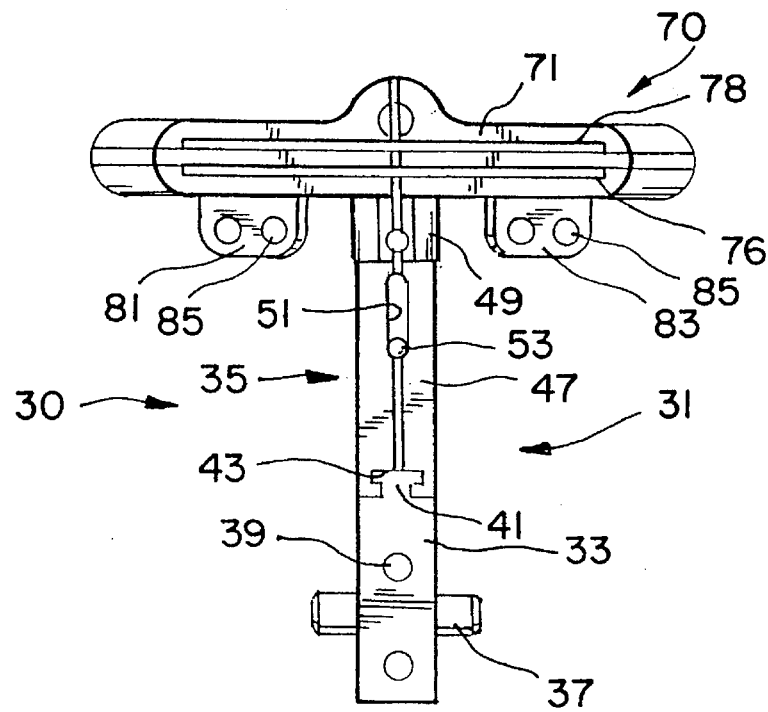
FIG. 7 shows a top view of the present invention with the stem structure in the retracted configuration.

With particular reference to FIGS. 6 and 7, it is seen that the stem structure 31 includes a groove 42 (second groove portion) which is aligned with a groove 91 (first groove portion) formed in the top surface 71 of the saw guide 70. In the preferred embodiment of the present invention, the aligned grooves 42 and 91 are approximately 1/16 of an inch in width and indicate the actual center of the instrument. The grooves 42 and 91 are parallel with the axis of elongation of the stem structure 31. In the preferred embodiment of the present invention, the grooves 42 and 91 are filled with titanium dioxide or another oxide of titanium which glows in the presence of a laser beam. While the grooves 42 and 91 may be used with conventional alignment systems to help facilitate alignment of the instrument 30 on the distal femur, the use of a titanium oxide in the grooves 42 and 91 makes them particularly susceptible to interaction with a laser alignment system. Through the use of a laser alignment system, when the instrument 30 is properly aligned, the titanium dioxide within the grooves 42 and 91 will glow clearly showing the surgeon proper alignment.

Figure 3:
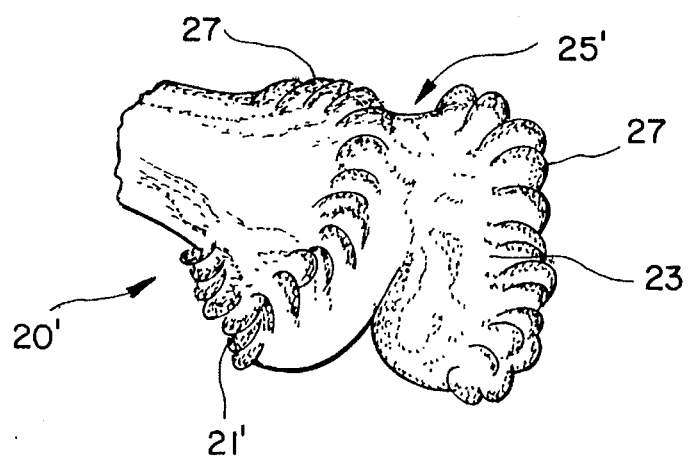
FIG. 3 shows a perspective view of a femur exhibiting osteophytic build-up of arthritic bone.
Figure 8:
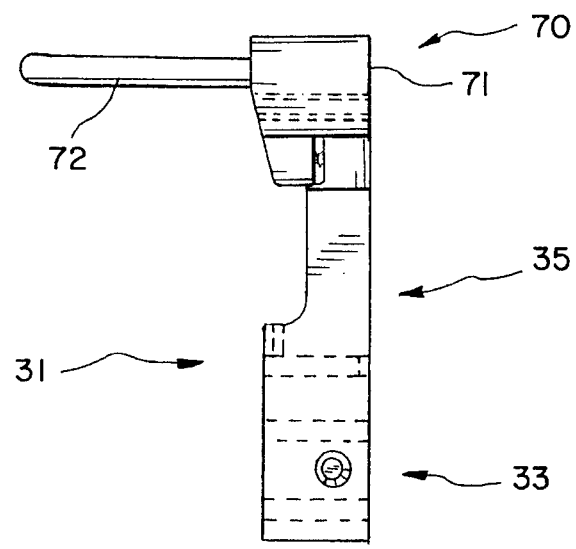
FIG. 8 shows a side view of the present invention with the proximal and distal ends of the stem structure aligned with one another.
Figure 9:
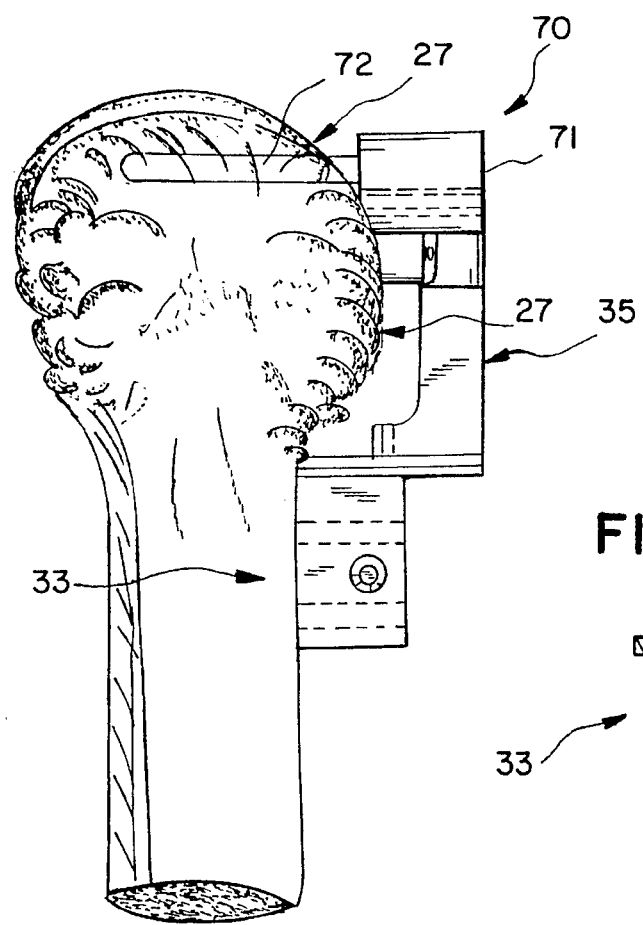
FIG. 9 shows a side view of the present invention with the proximal end of the stem structure aligned in the posterior direction with respect to the distal end of the stem structure, shown attached to a distal femur exhibiting osteophytic bone buildup.
Figure 10:
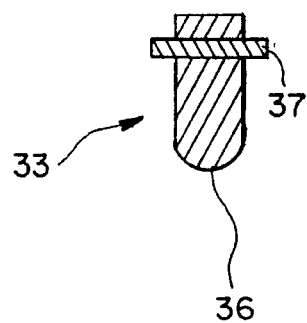
FIG. 10 shows a cross-sectional view along the line X—X of FIG. 6.

FIGS. 8 and 9 show two positions of adjustment of the proximal portion 33 of the stem structure 31 with respect to the distal portion 35 thereof. FIG. 8 shows the portions 33 and 35 axially aligned. FIG. 9 shows the proximal portion 33 aligned in the posterior direction with respect to the distal portion 35. Such alignment is also shown in FIG. 9 which shows the distal femur 20' corresponding to that which is depicted in FIG. 3 including the osteophytic build-up 27 of arthritic bone. As shown in FIG. 9, the saw guide 70 is properly positioned with the proximal end 47 of the distal end 49 of the stem structure 31 extended with respect thereto. The proximal portion 33 of the stem structure 31 is seen to be aligned in the posterior direction so that it engages the anterior femoral cortex proximal to the osteophytic anterior femoral condyles. In this way, firm fixation through the use of pins may be accomplished.

In the preferred embodiment of the present invention, the undersurface 73 of the cutting head is angulated to approximate the curvature of the superior distal femoral condyles. Such angulation provides more contact on the distal femoral condyle and better purchase thereon.

Figure 1:
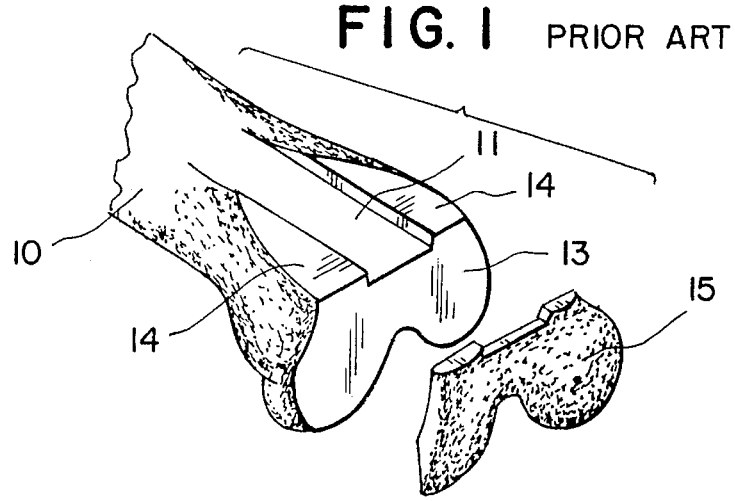
FIG. 1 corresponds to FIG. 5 of Applicant's prior U.S. Pat. No. 4,773,407 and FIG. 5 of Applicant's prior U.S. Pat. No. 4,907,578 and shows the prior art method of filing a surface on the anterior femoral cortex to receive a resector guide.
Figure 2:
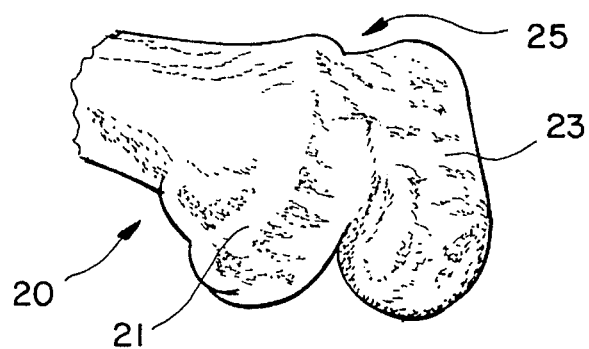
FIG. 2 shows a perspective view of a healthy distal femur.

As should now be understood, through the use of the present invention, it is not necessary to file a surface such as the surface 11 illustrated in FIG. 1 to receive the inventive instrument thereon. Furthermore, use of the present invention also renders unnecessary the resection designated by the reference numeral 14 in FIG. 1 prior to attachment of the inventive instrument 30. The resection resulting in the surface 14 can be carried out subsequently. Thus, use of the present invention reduces the invasiveness of surgery, reduces the time of the surgical procedure and, thus, increases the safety thereof.

Accordingly, an invention has been disclosed in terms of a preferred embodiment thereof which fulfills each and every one of the objects of the invention as set forth hereinabove and provides a new and useful improved distal femoral resector guide of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A distal femoral resector guide, for resecting a femur having an outer surface comprising:

a) a body including an elongated stem structure having a proximal end, a distal end and an axis of elongation and a saw guide attached at said stem structure distal end to form a T-shaped configuration;

b) said stem structure having adjustment means for controllably elongating said stem structure, and including a bone engageable surface convexly radiused in a plane of a cross-section of said stem structure perpendicular to said axis of elongation of said stem structure whereby when said saw guide is engaged with the distal femur to guide resection of the distal femur, said convexly radiused surface of said stem structure is adapted to engage said femur outer surface with a line contact regardless of a degree of slope of an associated anterior femoral cortex.

2. The guide of claim 1, wherein said adjustment means comprises first adjustment means, and said stem structure further including second adjustment means for adjusting a position of a portion of said stem structure in an anterior-posterior direction.

3. The guide of claim 2, wherein said portion comprises a proximal portion.

4. The guide of claim 1, wherein said adjustment means includes telescoping structure.

5. The guide of claim 4, wherein said adjustment means includes means for preventing relative rotation between said stem structure and saw guide.

6. The guide of claim 5, wherein said means for preventing relative rotation includes a pin extending outwardly from an inner telescoping member received in a slot in an outer telescoping member.

7. A distal femoral resector guide for resecting a femur having an outer surface, comprising:

a) a body including an elongated stem structure having a proximal end, a distal end and an axis of elongation, and a saw guide attached at said stem structure distal end to form a T-shaped configuration;

b) said stem structure having adjustment means for adjusting a position of a portion of said stem structure in an anterior-posterior direction, and including a bone engageable surface convexly radiused in a plane of a cross-section of said stem structure perpendicular to said axis of elongation of said stem structure whereby when said saw guide is engaged with the distal femur to guide resection of the distal femur, said convexly radiused surface of said stem structure is adapted to engage said femur outer surface with a line contact regardless of a degree of slope of an associated anterior femoral cortex.

8. A distal femoral resector guide, comprising:

a) a body having a T-shaped configuration including an elongated stem structure having a proximal end and a distal end and a saw guide orthogonally attached at said stem structure distal end and having a guide slot extending therethrough;

b) said guide having a top surface extending substantially across said saw guide, said guide slot extending continuously from adjacent one side of said top surface to adjacent another side of said top surface, said top surface having a first groove therein parallel with an axis of elongation of said stem structure, said first groove crossing said guide slot and comprising alignment means for aligning said guide on a distal femur, and further including a second groove on said stem structure aligned with said first groove.

9. The guide of claim 8, wherein said groove contains an oxide of titanium.

10. The guide of claim 9, wherein said oxide of titanium comprises titanium dioxide.

* * * * *